US006486386B1

(12) United States Patent
Christensen

(10) Patent No.: US 6,486,386 B1
(45) Date of Patent: Nov. 26, 2002

(54) INBRED SWEET CORN LINE I778S

(75) Inventor: Kenneth Paul Christensen, Nampa, ID (US)

(73) Assignee: Harris Moran Seed Company, Modesto, CA (US)

( * ) Notice: Subject to any disclaimer, the term of this patent is extended or adjusted under 35 U.S.C. 154(b) by 13 days.

(21) Appl. No.: 09/619,613

(22) Filed: Jul. 19, 2000

(51) Int. Cl.$^7$ .............................. A01H 1/00; A01H 1/02; A01H 5/00; A01H 5/10; C12N 5/04
(52) U.S. Cl. .................... 800/320.1; 800/263; 800/265; 800/275; 800/278; 800/279; 800/284; 800/300.1; 800/301; 800/302; 800/303; 435/412; 435/419; 435/421; 435/424; 435/430; 435/430.1
(58) Field of Search ............................... 800/320.1, 298, 800/275, 266, 268, 301, 302, 303, 263, 265, 300.1, 278, 279, 284; 435/412, 424, 430, 430.1, 419, 421

Primary Examiner—David T. Fox
(74) Attorney, Agent, or Firm—Jondle & Associates PC

(57) ABSTRACT

An inbred sweet corn line, designated I778S, is disclosed. The invention relates to the seeds of inbred corn line I778S, to the plants of inbred corn line I778S and to methods for producing a corn plant produced by crossing the inbred line I778S with itself or another corn line. The invention further relates to hybrid corn seeds and plants produced by crossing the inbred line I778S with another corn line.

20 Claims, No Drawings

INBRED SWEET CORN LINE I778S

BACKGROUND OF THE INVENTION

The present invention relates to a new and distinctive sweet corn inbred line, designated I778S. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, improved flavor, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s). The best lines are candidates for new commercial cultivars; those elite in traits are used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior sweet corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new sweet corn inbred line.

The development of commercial sweet corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complimentary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of hetero-zygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parents is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Sweet corn is an important and valuable vegetable crop. Thus, a continuing goal of plant breeders is to develop stable, high yielding sweet corn hybrids that are agronomically sound. The reasons for this goal are obviously to maximize the amount of ears and kernels produced on the land used and to supply food for humans. To accomplish this goal, the sweet corn breeder must select and develop sweet corn plants that have the traits that result in superior parental lines for producing hybrids.

SUMMARY OF THE INVENTION

According to the invention, there is provided a novel inbred corn line, designated I778S. This invention thus relates to the seeds of inbred corn line I778S, to the plants of inbred corn line I778S and to methods for producing a corn plant produced by crossing the inbred line I778S with itself or another corn line. This invention further relates to hybrid corn seeds and plants produced by crossing the inbred line I778S with another corn line.

The inbred corn plant of the invention may further comprise, or have, a cytoplasmic factor that is capable of conferring male sterility. Parts of the corn plant of the present invention are also provided, such as e.g., pollen obtained from an inbred plant and an ovule of the inbred plant.

In one aspect, the present invention provides for single gene converted plants of I778S. The single transferred gene may preferably be a dominant or recessive allele. Preferably, the single transferred gene will confer such traits as male sterility, herbicide resistance, insect resistance, resistance for bacterial, fungal, or viral disease, male fertility, enhanced nutritional quality, and industrial usage. The single gene may be a naturally occurring maize gene or a transgene introduced through genetic engineering techniques.

In another aspect, the present invention provides regenerable cells for use in tissue culture or inbred corn plant I778S. The tissue culture will preferably be capable of regenerating plants having the physiological and morphological characteristics of the foregoing inbred corn plant, and of regenerating plants having substantially the same genotype as the foregoing inbred corn plant. Preferably, the regenerable cells in such tissue cultures will be embryos, protoplasts, meristematic cells, callus, pollen, leaves, anthers, roots, root tips, silk, kernels, ears, cobs, husks or stalks. Still further, the present invention provides corn plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Allele. The allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Daily heat unit value. The daily heat unit value is calculated as follows: (The maximum daily temperature+the minimum daily temperature)/2 minus 50. All temperatures are in degrees Fahrenheit. The maximum temperature threshold is 86°, if temperatures exceed this, 86 is used. The minimum temperature threshold is 50°, if temperatures go below this, 50 is used.

Endosperm Type. Endosperm type refers to endosperm genes and types such as starch, sugary alleles (su1, su2, etc.), sugary enhancer or extender, waxy, amylose extender, dull, brittle alleles (bt1, bt2, etc.), other sh2 alleles, and any combination of these.

Essentially all the physiological and morphological characteristics. A plant having essentially all the physiological and morphological characteristics means a plant having the physiological and morphological characteristics, except for the characteristics derived from the converted gene.

HTU. HTU is the summation of the daily heat unit value calculated from emergence to harvest.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

DETAILED DESCRIPTION OF THE INVENTION

Inbred sweet corn line I778S is a yellow sweet corn with a sh2 endosperm and superior characteristics, and provides an excellent parental line in crosses for producing first generation ($F_1$) hybrid sweet corn.

I778S was developed from a related cross of breeding line P3EGTR7SH×sweet corn inbred I301S. This cross was then selfed and selected using the pedigree method of plant breeding. Resistance to Common Rust and Maize Dwarf Mosaic and tolerance to Northern Leaf Blight were selected during the inbreeding process.

Inbred sweet corn line I778S has the following morphologic and other characteristics (based primarily on data collected at Nampa, Id.).

Variety Description Information

1. TYPE: Inbred
2. REGION WHERE DEVELOPED: Nampa, Id.
3. VIGOR: (1=very weak–5=very strong): 3.5
4. MATURITY:

|  | Days |
| --- | --- |
| From planting to 50% of plants in tassel | 67 |
| From planting to 50% of plants in silk | 71 |

5. PLANT:
   Plant Height (to tassel tip): 139.7 cm
   Ear Height (to base of top ear): 50.04 cm
   Average number of Tillers: 2.5
   Average Number of Ears per Stalk: 1.2
   Anthocyanin Markings: None
6. LEAF:
   Width of Ear Node Leaf: 8.05 cm
   Length of Ear Node Leaf: 83.06 cm
   Leaf Angle from 2nd leaf above ear: 40°
   Leaf Sheath Pubescence (1=none–5=peach fuzz): 2
   Marginal waves (1=none–5=many): 5
   Longitudinal Creases (1=none–5=many): 1
7. TASSEL:
   Number of Tassel Branches: 19.5
   Branch Angle from Central Spike: 40°
   Tassel Length (from top leaf collar to tassel top): 32.55 cm
   Anther Color: Yellow
   Glume Color: Green
8. EAR:
   Silk color (3 days after emergence): Yellow
   Husk Extension: 10.1 cm
   Number of flag leaves: 3.5
   Average length of flag: 3.4 cm
   Average width of flag: 1.25 cm
   Ear Length: 17.05 cm
   Ear Diameter at mid-point: 3.9 cm
   Number of Kernel Rows: 14.8
   Row Straightness (1=very scrambled–5=perfectly straight): 3
   Shank Length: 14.0 cm
   Shape: Moderate taper, some flat tips
9. KERNEL:
   Color: Yellow
   Endosperm Type: sh2
10. COB:
    Cob Color: White, slight green
11. DISEASE RESISTANCE
    Rating (1=susceptible–5=resistant)
    4.8 Common Rust
    4.0 Maize Dwarf Mosaic
    2.7 Northern Leaf Blight
    2.5 Stewart's Wilt Resistance This invention is also directed to methods for producing a corn plant by crossing a first parent corn plant with a second parent corn plant, wherein the first or second corn plant is the inbred corn plant from the line I778S. Further, both first and second parent corn plants may be from the inbred line I778S. Therefore, any methods using the inbred corn line I778S are part of this invention: selfing, backcrosses, hybrid breeding, and crosses to populations. Any plants produced using inbred corn line I778S as a parent are within the scope of this invention. Advantageously, the inbred corn line is used in crosses with other corn varieties to produce first generation ($F_1$) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like.

The present invention contemplates a corn plant regenerated from a tissue culture of an inbred (e.g., I778S) or hybrid plant of the present invention. As is well known in the art, tissue culture of corn can be used for the in vitro regeneration of a corn plant. By way of example, a process of tissue culturing and regeneration of corn is described in European Patent Application, publication 160,390, the disclosure of which is incorporated by reference. Corn tissue culture procedures are also described in Green & Rhodes (I 982) and Duncan, et al., (1985). The study by Duncan et al., (1985) indicates that 97 percent of cultured plants produced calli capable of regenerating plants. Subsequent studies have shown that both inbreds and hybrids produced 91 percent regenerable calli that produced plants.

Other studies indicate that non-traditional tissues are capable of producing somatic embryogenesis and plant regeneration. See, e.g., Songstad et al., (1988); Rao et al., (1986); and Conger et al., (1987), the disclosures of which are incorporated herein by reference. Regenerable cultures may be initiated from immature embryos as described in PCT publication WO 95/06128, the disclosure of which is incorporated herein by reference.

Thus, another aspect of this invention is to provide for cells which upon growth and differentiation produce the inbred line I778S.

I778S is a yellow seeded sh2 sweet corn inbred. The background of I778S is similar to that of I701S. General ear shape, kernel color tint, seed quality, plant and tassel style is reflective of I701S. The foliage of I778S is dark green and the variety has a very strong Maize Dwarf Mosaic Virus resistance and possesses the Rp1d gene for common rust resistance. I778S expresses a moderate reaction to Northern Corn Leaf Blight infection. I778S is a main season inbred and is well adapted for use as a female or male in seed production. This sweet corn inbred contributes to high yield and high cut kernel recovery in processing hybrids.

The inbred has shown uniformity and stability. It has been self-pollinated and ear-rowed a sufficient number of generations, with careful attention to uniformity of plant type to ensure homozygosity and phenotypic stability. The line has been increased both by hand and sibbed in isolated fields with continued observations for uniformity. No variant traits have been observed or are expected in I778S.

Table

In the table that follows, the traits and characteristics of inbred sweet corn line I778S are given in hybrid combination along with data on commercial check hybrids. The first hybrid listed in the table contains I778S as one parent. Crisp N Sweet 710 is a commercial check hybrid. Information for the hybrids includes the following traits:

In the Tables, Columns 1 and 2 list the Hybrid and location where grown.

Column 3 shows the heat units (HTU) for the hybrid and commercial check.

Column 4 shows the yield (Yield) in tons of green corn or green weight per acre for the hybrid and commercial check.

Column 5 gives the cut corn (Cut Corn) in tons of kernels cut from the cobs per acre for the hybrid and commercial check.

Column 6 gives the cases per acre (Case/Acre) of canned product per acre for the hybrid and commercial check.

Column 7 is the percent of recovery (% Recov) of cut corn per yield for the hybrid and commercial check.

Column 8 represents the percent of moisture (% H20) of the kernels at harvest for the hybrid and commercial check.

| Yield Data for 1998 and 1999 | | | | | | | |
|---|---|---|---|---|---|---|---|
| Hybrid | Location | HTU | Yield | Cut Corn | Case/ Acre | % Re- cov | % H20 |
| 1778S × 1816S | LeSueur, MN | 1828 | 8.3 | 3.4 | 477 | 41.0 | 77.0 |
| 1778S × 1816S | Sun Prairie, WI | 1905 | 6.7 | 1.9 | 259 | 27.6 | 76.6 |
| 1778S × 1816S | Mendota, IL | 1820 | 6.1 | 1.8 | 253 | 29.7 | 77.7 |
| 1778S × 1816S | LeSueur, MN | 2010 | 11.6 | 2.9 | 420 | 25.3 | 77.7 |
| 1778S × 1816S | Sun Prairie, WI | 1763 | 7.8 | 1.6 | 219 | 20.1 | 78.7 |
| 1778S × 1816S | Mendota, IL | 1682 | 4.8 | 1.3 | 183 | 27.4 | 77.0 |
| Average | | 1834 | 7.6 | 2.2 | 302 | 28.5 | 77.5 |
| CrispNSweet 710 | LeSueur, MN | 1842 | 6.6 | 2.2 | 308 | 33.0 | 78.8 |
| CrispNSweet 710 | Sun Prairie, WI | 1700 | 6.0 | 1.6 | 223 | 26.6 | 78.7 |
| CrispNsweet 710 | Mendota, IL | 1781 | 5.1 | 1.6 | 223 | 31.6 | 78.3 |
| CrispNSweet 710 | LeSueur, MN | 1962 | 8.0 | 2.8 | 313 | 27.2 | 78.2 |
| CrispNSweet 710 | Sun Prairie, WI | 1737 | 6.4 | 1.5 | 205 | 22.9 | 78.5 |
| CrispNSweet 710 | Mendota, IL | 1672 | 3.3 | 1.0 | 142 | 30.8 | 78.0 |
| Average | | 1782 | 5.9 | 1.8 | 236 | 28.7 | 78.4 |

When the term inbred corn plant is used in the context of the present invention, this also includes any single gene conversions of that inbred. The term single gene converted plant as used herein refers to those corn plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental corn plants for that inbred. The parental corn plant which contributes the gene for the desired characteristic is termed the nonrecurrent or donor parent. This terminology refers to the fact that the nonrecurrent parent is used one time in the backcross protocol and therefore does not recur. The parental corn plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

A further aspect of the invention relates to tissue culture of corn plants designated I778S. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, kernels, ears, cobs, leaves, husks, stalks, roots, root tips, anthers, silk and the like. In a preferred embodiment, tissue culture is embryos, protoplast, meristematic cells, pollen, leaves or anthers. Means for preparing and maintaining plant tissue culture are well known in the art. By way of example, a tissue culture comprising organs such as tassels or anthers, has been used to produce regenerated plants. (See U.S. Pat. Nos. 5,445,961; 5,322,789; 5,948,957 and 5,969,212, the disclosures of which are incorporated herein by reference).

Deposit Information

A deposit of the Harris Moran Seed Company inbred sweet corn line I778S diclosed above and recited in the appended claims has been made withe the American Type Culture Collection (ATCC). 10801 University Boulevard, Manassas, Va. 20110. The date of deposit was Jul. 22, 2002. The deposit of 2,000 seeds were taken from the same deposit maintained by Harris Moran Seed Company since prior to the filing date of this application. All restrictions upon the deposit have been removed, and the deposit is intended to meet all of the requirements of 37 C.F.R. 1.801-1.809. The ATCC accession number is PTA—4560. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred corn seed designated I778S, a sample of said seed having been deposited under ATCC Accession No. PTA—4560.

2. A corn plant, or parts thereof, produced by growing the seed of claim 1.

3. Pollen of the plant of claim 2.

4. An ovule of the plant of claim 2.

5. The corn plant of claim 2, wherein said plant further comprises a genetic factor conferring male sterility.

6. A tissue culture of regenerable cells of a corn plant of inbred line I778S, wherein the tissue regenerates plants capable of expressing all the morphological and physiological characteristics of the inbred line I778S; a sample of said seed having been deposited under ATCC Acession No. PTA—4560.

7. A tissue culture according to claim 6, cells or protoplasts of the tissue culture being from a tissue selected from the group consisting of leaves, pollen, embryos, roots, root tips, anthers, silks, flowers, kernels, ears, cobs, husks, and stalks.

8. A method for producing a hybrid corn seed comprising crossing a first inbred parent corn plant with a second inbred parent corn plant and harvesting the resultant hybrid corn seed, wherein said first or second parent corn plant is the corn plant of claim 2.

9. A hybrid corn seed produced by the method of claim 8.

10. A hybrid corn plant, or parts thereof, produced by growing said hybrid corn seed of claim 9.

11. Corn seed produced by growing said hybrid corn plant of claim 10.

12. A corn plant, or parts thereof, produced from seed of claim 11.

13. A method for producing a hybrid corn seed comprising crossing an inbred plant according to claim 2 with another, different corn plant.

14. A hybrid corn seed produced by the method of claim 13.

15. A hybrid corn plant, or its parts, produced by growing said hybrid corn seed of claim 14.

16. Corn seed produced from said hybrid corn plant of claim 15.

17. A corn plant, or its parts, produced from the corn seed of claim 16.

18. The corn plant of claim 2, further comprising a single gene conversion.

19. The single gene conversion corn plant of claim 18, where the gene is selected from the group consisting of: a transgene, a dominant allele and a recessive allele.

20. The single gene conversion corn plant of claim 19, where the gene confers a characteristic selected from the group consisting of: herbicide resistance; insect resistance; resistance to bacterial, fungal, or viral disease; male sterility; endosperm type and improved nutritional quality.

* * * * *